US012788498B2

(12) United States Patent
Dickhans

(10) Patent No.: US 12,788,498 B2
(45) Date of Patent: Nov. 10, 2026

(54) SYSTEMS AND METHODS FOR ACTIVE TRACKING OF ELECTROMAGNETIC NAVIGATION BRONCHOSCOPY TOOLS WITH SINGLE GUIDE SHEATHS

(71) Applicant: Covidien LP, Mansfield, MA (US)

(72) Inventor: William J. Dickhans, Longmont, CO (US)

(73) Assignee: Covidien LP, Mansfield, MA (US)

( * ) Notice: Subject to any disclaimer, the term of this patent is extended or adjusted under 35 U.S.C. 154(b) by 199 days.

(21) Appl. No.: 18/430,192

(22) Filed: Feb. 1, 2024

(65) Prior Publication Data

US 2024/0307126 A1 Sep. 19, 2024

Related U.S. Application Data

(60) Provisional application No. 63/453,105, filed on Mar. 18, 2023.

(51) Int. Cl.
*A61B 34/20* (2016.01)
*A61B 1/267* (2006.01)
(Continued)

(52) U.S. Cl.
CPC ............ *A61B 34/20* (2016.02); *A61B 1/2676* (2013.01); *A61B 34/10* (2016.02); *A61B 34/25* (2016.02);
(Continued)

(58) Field of Classification Search
CPC ......... A61B 34/20; A61B 34/10; A61B 34/25; A61B 90/361; A61B 90/37; A61B 1/2676;
(Continued)

(56) References Cited

U.S. PATENT DOCUMENTS 7,699,829 B2 4/2010 Harris et al.
7,905,864 B2 3/2011 Ponzi
(Continued)

FOREIGN PATENT DOCUMENTS

WO WO-2021163039 A1 * 8/2021 ............. A61B 90/39

OTHER PUBLICATIONS

Extended European search report issued in European Patent Application No. 24164005.1 dated Jul. 30, 2024.

*Primary Examiner* — Patricia J Park
(74) *Attorney, Agent, or Firm* — Weber Rosselli & Cannon LLP

(57) ABSTRACT

Systems and methods for accurately navigating tools through a luminal network to a target use fixed length tools to minimize use of radiographic imaging and thus exposure to radiation. The systems and methods involve receiving computed tomography (CT) image data, generating a three-dimensional (3D) model based on the CT image data, causing display of the 3D model, and receiving a location of the target in the 3D model. The systems and methods also involve receiving information of a tool to be guided through an extended working channel (EWC) including a location sensor, determining a location of the tool after the tool is guided through and fixed in place with respect to the EWC, causing display of a virtual tool in the 3D model based on location information from the location sensor and the tool information, and causing display of advancement of the tool to the target in the 3D model based on the location information and the tool information.

19 Claims, 5 Drawing Sheets

200

(51) Int. Cl.
*A61B 34/00* (2016.01)
*A61B 34/10* (2016.01)
*A61B 90/00* (2016.01)

(52) U.S. Cl.
CPC ............ *A61B 90/361* (2016.02); *A61B 90/37* (2016.02); *A61B 2034/102* (2016.02); *A61B 2034/105* (2016.02); *A61B 2034/107* (2016.02); *A61B 2034/2051* (2016.02); *A61B 2034/252* (2016.02); *A61B 2090/3612* (2016.02); *A61B 2090/367* (2016.02); *A61B 2090/3764* (2016.02)

(58) Field of Classification Search
CPC ........ A61B 2034/102; A61B 2034/105; A61B 2034/107; A61B 2034/2051; A61B 2034/252; A61B 2090/3612; A61B 2090/367; A61B 2090/3764
See application file for complete search history.

(56) References Cited

U.S. PATENT DOCUMENTS

| | | | | |
|---|---|---|---|---|
| 8,491,619 | B2 | 7/2013 | Breznock | |
| 10,265,507 | B2 | 4/2019 | Belson | |
| 11,007,329 | B2 | 5/2021 | Fischell et al. | |
| 2008/0119846 | A1 | 5/2008 | Rioux | |
| 2008/0147040 | A1 | 6/2008 | Dikshteyn | |
| 2008/0319314 | A1 | 12/2008 | Hill et al. | |
| 2015/0119875 | A1 | 4/2015 | Fischell et al. | |
| 2017/0156685 | A1 * | 6/2017 | Dickhans | A61B 6/032 |
| 2018/0055574 | A1 | 3/2018 | Krimsky et al. | |
| 2018/0318009 | A1 * | 11/2018 | Sohlden | A61B 90/96 |
| 2018/0344389 | A1 * | 12/2018 | Gonzalez | A61B 8/481 |
| 2019/0374130 | A1 * | 12/2019 | Bydlon | A61B 10/04 |
| 2020/0100843 | A1 * | 4/2020 | Koyrakh | A61B 5/1495 |
| 2021/0248922 | A1 * | 8/2021 | Gordon | G09B 9/00 |
| 2022/0015837 | A1 * | 1/2022 | Krimsky | A61B 34/10 |

* cited by examiner

200

SYSTEMS AND METHODS FOR ACTIVE TRACKING OF ELECTROMAGNETIC NAVIGATION BRONCHOSCOPY TOOLS WITH SINGLE GUIDE SHEATHS

CROSS-REFERENCE TO RELATED APPLICATION

This application claims the benefit of, and priority to U.S. Provisional Patent Application Ser. No. 63/453,105, filed on Mar. 18, 2023, the entire content of each of which is incorporated by reference herein.

FIELD

The disclosed technology is generally related to intraluminal navigation and therapy systems and methods that minimize exposure to radiation from radiographic imaging while navigating a medical tool to a target.

BACKGROUND

There are several commonly applied medical methods, such as endoscopic procedures or minimally invasive procedures, for treating various maladies affecting organs including the liver, brain, heart, lungs, gall bladder, kidneys, and bones. Often, one or more imaging modalities, such as magnetic resonance imaging (MRI), ultrasound imaging, computed tomography (CT), or fluoroscopy are employed by clinicians to identify and navigate to areas of interest within a patient and to a target for biopsy or treatment. In some procedures, preoperative scans may be utilized for target identification and intraoperative guidance. In some cases, real time imaging or intraoperative imaging may also be required to obtain a more accurate and current image of the target area and an endoluminal medical tool used to biopsy or treat tissue in the target area. Furthermore, real time image data displaying the current location of a medical device with respect to the target and its surroundings may be needed to navigate the medical device to the target in a safe and accurate manner (e.g., without causing damage to other organs or tissue). Real-time, intraoperative imaging, however, may expose the patient to unnecessary and/or potentially unhealthy amounts of X-ray radiation.

An endoscopic approach has proven useful in navigating to areas of interest within a patient, and particularly so for areas within luminal networks of the body such as the lungs. To enable the endoscopic approach, and more particularly the bronchoscopic approach in the lungs, endobronchial navigation systems have been developed that use previously acquired MRI data or CT image data to generate a three dimensional (3D) rendering, model, or volume of the particular body part such as the lungs.

The resulting volume generated from the MRI scan or CT scan is then utilized to create a navigation plan to facilitate the advancement of a navigation catheter (or other suitable medical tool) through a bronchoscope and a branch of the bronchus of a patient to an area of interest. A locating or tracking system, such as an electromagnetic (EM) tracking system, may be utilized in conjunction with, for example, CT data, to facilitate guidance of the navigation catheter through branches of the bronchus to the area of interest. In certain instances, the navigation catheter may be positioned within one of the airways of the branched luminal networks adjacent to, or within, the area of interest to provide access for one or more medical tools.

However, a 3D volume of a patient's lungs, generated from previously acquired scans, such as CT scans, may not provide a basis sufficient for accurate guiding of medical devices or tools to a target during a navigation procedure. In some cases, the inaccuracy is caused by deformation of the patient's lungs during the procedure relative to the lungs at the time of the acquisition of the previously acquired CT data. This deformation (CT-to-Body divergence) may be caused by many different factors including, for example, changes in the body when transitioning from between a sedated state and a non-sedated state, the bronchoscope changing the patient's pose, the bronchoscope pushing the tissue, different lung volumes (e.g., the CT scans are acquired during inhale while navigation is performed during breathing), different beds, different days, etc. This deformation may lead to significant motion of a target, making it challenging to align a medical tool with the target in order to safely and accurately biopsy or treat tissue of the target.

Thus, systems and methods are needed to account for motion of a patient during an in vivo navigation and biopsy or treatment procedures. Furthermore, to navigate a medical tool safely and accurately to a remote target and biopsy or treat the remote target with the medical tool, either by a surgical robotic system or by a clinician using a guidance system, the systems should track the tip of the medical tool during the motion of the patient's body, e.g., motion of the patient's chest during respiration, while minimizing the patient's exposure to intraoperative X-ray radiation.

SUMMARY

The techniques of this disclosure generally relate to positioning a tool within an extended working channel (EWC) such that a distal portion of the tool extends a predetermined distance from a distal end portion of the EWC, tracking the distal portion the tool based on electromagnetic (EM) signals from at least one EM sensor disposed on a distal portion of the EWC, and navigating the EWC and the tool together towards a target based on the tracked distal portion of the tool. This configuration minimizes or eliminates use of intraprocedural imaging and hence minimizes or eliminates exposure to harmful amounts of radiation.

In one aspect, this disclosure provides a system for navigating to a target via a luminal network of a patient. The system includes an extended working channel (EWC) including a location sensor disposed at a distal portion of the EWC, at least one processor, and a memory coupled to the at least one processor. The memory has stored thereon instructions, which when executed by the at least one processor, cause the at least one processor to receive preprocedural computed tomography (CT) images, generate a three-dimensional (3D) model based on the CT images, and cause display of the 3D model in a user interface on a display operatively coupled to the at least one processor. The instructions, when executed by the at least one processor, also cause the at least one processor to receive an indication of a location of a target in the CT images, cause display of the location of the target in the 3D model, and generate a pathway plan to the target for navigation of the EWC.

The instructions, when executed by the at least one processor, also cause the at least one processor to receive location information from the location sensor as the EWC is navigated through a luminal network of a patient, register the 3D model with the luminal network of the patient based on the location information, cause display of the location of the location sensor within the 3D model that substantially corresponds to the location of the location sensor within the luminal network of the patient, and cause display of the navigation of the extended working channel following the pathway plan to a location near the target. The instructions, when executed by the at least one processor, also cause the at least one processor to receive tool information of a tool disposed within the EWC, fixed relative to the EWC, and having a distal end portion extending distally beyond the distal end portion of the EWC, determine a location of a portion of the tool based on the location information from the location sensor, and cause display of a virtual tool in the 3D model according to the location information and the tool information; and cause display of advancement of the virtual tool into the target in the 3D model based on the location information and the tool information.

In aspects, implementations of the system may include one or more of the following features. The tool may include a locatable guide tool, which may include a second location sensor, an ablation tool, or a biopsy tool. The EWC may include an EWC handle. The tool may include a fixing member that mates with the EWC handle when the tool is disposed within the EWC and a distal portion of the tool extends beyond a distal portion of the EWC. The fixing member may fix the tool in place with respect to the EWC. The tool may include a handle for operating the tool.

A distal portion of the EWC may be curved. The instructions when executed by the at least one processor may cause the at least one processor to receive location information with six degrees of freedom. The instructions when executed by the at least one processor may cause the at least one processor to display a message prompting a user to lock a bronchoscope adapter, receive intraprocedural images, update a relative position of the target and the EWC in the 3D model based on the intraprocedural images, and display a message prompting the user to unlock a bronchoscope adapter.

The intraprocedural images may be C-arm fluoroscopic images, 3D fluoroscopic images, or cone beam CT images. The tool information may be a tool type, tool characteristics, or tool dimensions. The instructions when executed by the at least one processor may cause the at least one processor to determine a location of a distal portion of the tool by projecting the location information according to the tool information, and cause display of a portion of the virtual tool in the 3D model based on the location of the distal portion of the tool.

The system may include a tool memory coupled to the tool and configured to store the tool information, and a tool memory reader configured to read the tool information from the tool memory. The at least one processor may be in operative communication with the tool memory reader. The instructions when executed by the at least one processor may cause the at least one processor to receive the tool information from the tool memory reader.

In another aspect, this disclosure provides a method for navigating to a target via a luminal network. The method includes receiving computed tomography (CT) images, generating a three-dimensional (3D) model based on the CT images, and causing display of the 3D model in a user interface on a display. The method also includes receiving an indication of a location of a target in the CT images, causing display of the location of the target in the 3D model, and generating a pathway plan to the target for navigation of a catheter. The method also includes receiving location information from a location sensor disposed at a distal portion of the catheter, registering the 3D model with a luminal network of a patient based on the location information, and causing display of the location of the location sensor within the 3D model.

The method also includes causing the display of the navigation of the catheter following the pathway plan to a location near the target, and receiving tool information of a tool disposed within the catheter, fixed in place relative to the catheter, and having a distal end portion extending distally beyond the distal end portion of the catheter. The method also includes determining a location of a portion of the tool based on the location information from the sensor, causing display of at least a portion of the tool in the 3D model based on the location information and the tool information, and causing display of advancement of the tool to the target in the 3D model based on the location information and the tool information.

In aspects, implementations of the method may include one or more of the following features. The method may include displaying a distal end portion of the tool as the target is treated, ablated, sampled, or biopsied. Determining the location of the portion of the tool may include determining a location of a distal end portion of the tool by projecting the location information from the sensor to the distal end portion of the tool. The method may include receiving intraprocedural images of the catheter and the target, and updating a location of the catheter relative to the target in the 3D model based on the intraprocedural images.

Receiving the intraprocedural images may include receiving 2D fluoroscopic images, 3D fluoroscopic images, or cone beam CT images. The method may include causing display of at least a portion of the pathway plan, at least a portion of the tool, and the target on the intraprocedural images. The intraprocedural images may be captured at a decreased radiation dose.

In another aspect, this disclosure provides a system that includes a guide catheter, a sensor coupled to the guide catheter, and tools. The guide catheter is configured for insertion into a luminal network of a patient, and the sensor is configured to sense a location of a distal end portion of the guide catheter within the luminal network of the patient. The tools are configured to be inserted through the guide catheter such that a distal end portion of the tools extend distally beyond the distal end portion of the guide catheter. The tools are also configured to be fixed relative to the guide catheter during navigation of the guide catheter. The system also includes at least one processor, a display operatively coupled to the at least one processor, and a memory coupled to the at least one processor. The memory has stored thereon instructions, which when executed by the at least one processor, cause the at least one processor to cause display of a virtual target in a 3D model on the display, receive location information from the sensor in the luminal network of the patient, and cause display of navigation of a virtual guide catheter near the virtual target in the 3D model based on the location information.

The instructions, when executed by the at least one processor, also cause the at least one processor to determine tool information from a tool inserted through the guide catheter and fixed in place relative to the guide catheter, and determine a location of a distal portion of the tool. The instructions, when executed by the at least one processor, also cause the at least one processor to cause display, in the 3D model, the distal portion of a virtual tool based on the location information and the tool information, and cause display of operation of the virtual tool to perform a procedure on the virtual target in the 3D model based on updated location information and the tool information.

In aspects, implementations of the system may include one or more of the following features. The guide catheter may be a smart extended working channel, and the tools may include at least two of a locatable guide, a forceps, a biopsy needle, or an ablation antenna. The system may include a bronchoscope adapter configured to lock the guide catheter in place. The instructions, when executed by the at least one processor, may cause the at least one processor to receive intraprocedural images, update a position of the virtual target relative to the virtual guide catheter in the 3D model based on the intraprocedural images, and display a message prompting the user to unlock the bronchoscope adapter before performing a procedure with a tool of the tools.

The tools may include handles and the lengths from the distal end portions of the handles to the distal end portions of the tools may be the same lengths. The system may include an electromagnetic generator configured to generate an electromagnetic field. The sensor may be an EM sensor configured to sense the electromagnetic field and output an electromagnetic field signal indicating the location of the EM sensor.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
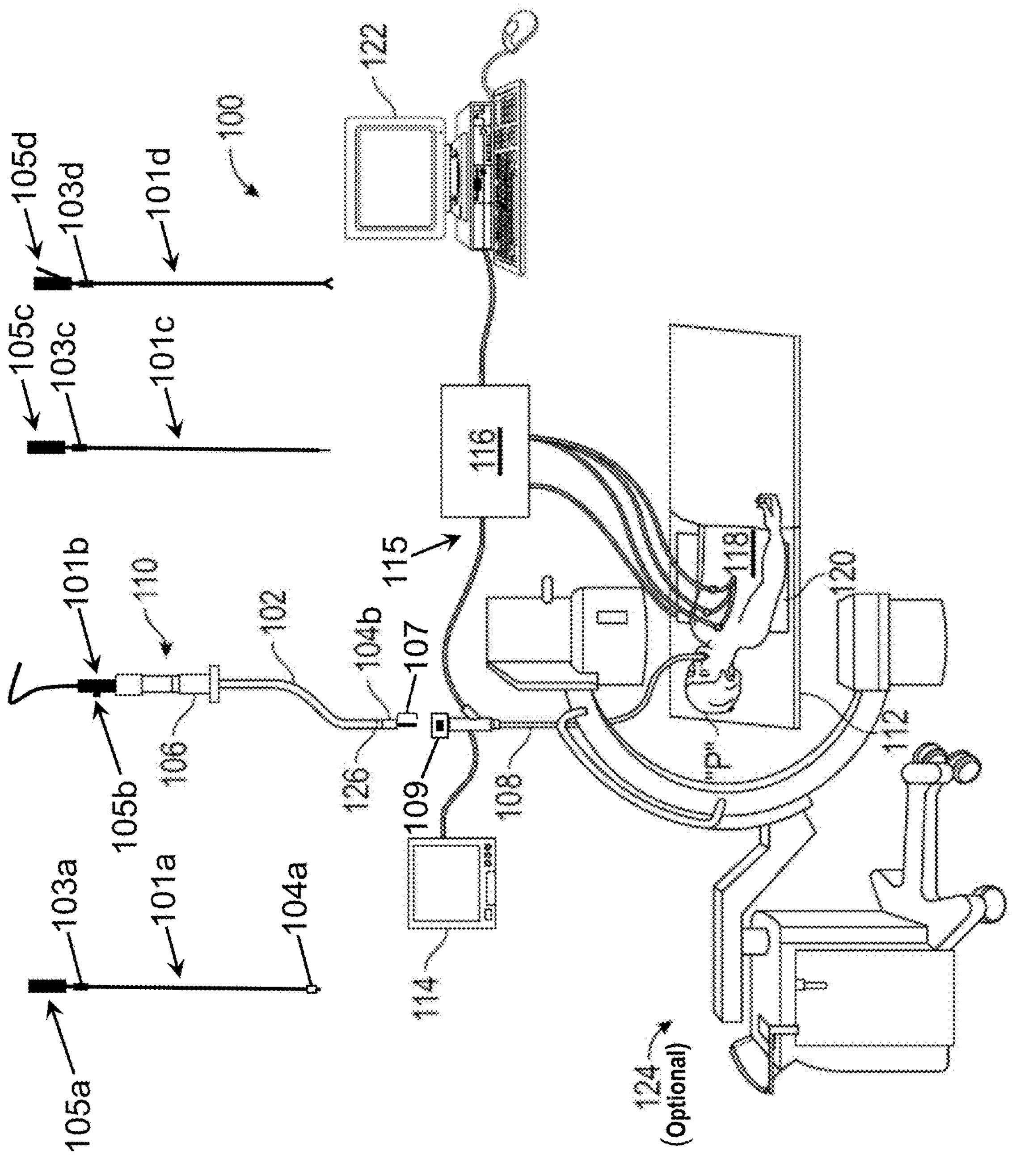
FIG. 1 is a perspective view that illustrates an electromagnetic navigation and imaging system in accordance with this disclosure.

According to systems and methods of this disclosure, an electromagnetic navigation (EMN) system is used to perform biopsies or treatment of lung lesions through a bronchoscope. The system uses a smart extended working channel (sEWC) as the guide catheter. The sEWC may include an electromagnetic (EM) sensor for determining the position of the sEWC. The sEWC is parked near the lesion, e.g., a few centimeters from the lesion, and tools are then extended from the end of the sEWC, and the lesion is sampled or treated. To understand where the tool is sampling, a C-arm fluoroscope is typically used for visualization. However, hospitals and clinicians are looking to reduce radiation from the C-arm fluoroscope as much as possible so as to extend the lives of patients as long as possible.

The systems and methods of this disclosure perform tool tracking with an EMN system, e.g., an electromagnetic navigation bronchoscopy (ENB) system, by only updating the tools that are used. The sEWC or guide catheter is guided to a target site, e.g., a lesion site, and is parked and locked into place using a bronchoscope adapter (BA) connected to the bronchoscope. The systems and methods of this disclosure may involve tools designed to be a fixed length so that once each tool is inserted into the sEWC, each tool protrudes a set amount or predetermined distance from the distal end portion of the sEWC. By having a distal portion of each tool protrude a set amount from the distal end portion of the sEWC, the amount of deflection of the distal portion of each tool is limited. Consequently, the distal portion of each tool is straight and/or rigid or is substantially straight and/or rigid such that at least the distal portion of each tool can be modeled and/or represented on EMN tracking screens or windows based on location information from an EM sensor disposed at a distal portion of the sEWC. In some aspects, the distal portions of each tool are designed to be rigid or substantially rigid, e.g., by using suitable materials or design configuration, to ensure accurate tracking of each tool relative to target tissue.

The systems and methods of this disclosure limit the amount of radiation from the use of a C-arm fluoroscope or other intraprocedural radiographic imaging modality to guide and place the sEWC near or at the target. When the clinician wants to take a biopsy or treat the target tissue, the BA is unlocked and the entire sEWC is moved until the tool is in the desired location and a sample of the target tissue can be taken or the target tissue can be treated. By moving the entire sEWC, the clinician can take the biopsy using EMN tracking instead of using a radiographic imaging modality that emits potentially harmful radiation. This allows for tool tracking using the EMN system for tissue biopsies and/or tissue treatment, which minimizes radiation to the patient and/or clinicians, and provides true 3D control of the tool compared to a 2D view with a fluoroscopic image captured by a C-arm fluoroscope or a 2D view with a radiographic image captured by a radiographic imaging modality.

FIG. 1 is a perspective view of an example of a system 100 for facilitating navigation of a medical device, e.g., a catheter, to a target via airways of the lungs. The system 100 may be further configured to construct fluoroscopic-based 3D volumetric data of the target area from intraprocedural 2D radiographic images, e.g., intraprocedural 2D fluoroscopic images, to confirm navigation of an sEWC to a desired location near the target area, where a tool may be placed through and extending out of the sEWC. In aspects, the imaging system 124 of the system 100 may include one or more of a C-arm fluoroscope, a cone-beam computed tomography (CBCT) imaging system, or a 3D fluoroscopic imaging system.

The system 100 may be further configured to facilitate approach of a medical device or tool to the target area and to determine the location of the medical tool with respect to the target by using electromagnetic navigation (EMN) of the sEWC. One such EMN system is the ILLUMISITE system currently sold by Medtronic PLC, though other systems for intraluminal navigation are considered within the scope of this disclosure.

One aspect of the system 100 is a software component for reviewing computed tomography (CT) image scan data that has been acquired separately from the system 100. The review of the CT image data allows a user to identify one or more targets, plan a pathway to an identified target (planning phase), navigate the sEWC 102 to the target (navigation phase) using a user interface running on a computer system 122, and confirming placement of a distal end portion of the sEWC 102 near the target using one or more electromagnetic (EM) sensors 104*b*, 126 disposed in or on the sEWC 102 at a predetermined position at or near the distal end portion of the sEWC 102. The target may be tissue of interest identified by review of the CT image data during the planning phase. Following navigation of the sEWC 102 near the target, a medical device, such as a biopsy tool, an access tool, or a therapy tool, e.g., a flexible microwave ablation catheter, is inserted into and fixed in place with respect to the sEWC 102 such that a distal end portion of the medical device extends a desired distance 107 beyond the distal end of the sEWC 102 and the sEWC 102 is further navigated using EM navigation to obtain a tissue sample, enable access to a target site, or apply therapy to the target using the medical device.

As shown in FIG. 1, the sEWC 102 is part of a catheter guide assembly 110. In practice, the sEWC 102 is inserted into a bronchoscope 108 for access to a luminal network of the patient P. Specifically, the sEWC 102 of catheter guide assembly 110 may be inserted into a working channel of bronchoscope 108 for navigation through a patient's luminal network. A bronchoscope adapter 109 is coupled to the proximal end portion of the bronchoscope. The bronchoscope adapter 109 may be the EDGE™ Bronchoscope Adapter, which is currently marketed and sold by Medtronic PLC. The bronchoscope adapter 109 is configured either to allow motion of the sEWC 102 through the working channel of the bronchoscope 108 (which may be referred to as an unlocked state of the bronchoscope adapter 109) or prevent motion of the sEWC 102 through the working channel of the bronchoscope (which may be referred to as an unlocked state of the bronchoscope adapter 109).

A locatable guide (LG) 101*a*, which may be a catheter and which may include a sensor 104*a* similar to the sensor 104*b* is inserted into the sEWC 102 and locked into position such that the LG sensor 104*a* extends a predetermined distance beyond the distal end portion of the sEWC 102. The tools 101*a*-101*d* of the same lengths which include a fixing member 103*a-d* such that when the fixing member 103*a*-103*d* of the tools 101*a*-101*d* engages, e.g., snaps in, with the proximal end portion of the handle 106 of the catheter guide assembly 110, the LG 101*a* extends a predetermined distance 107 beyond a distal tip or end portion of the sEWC 102. The predetermined distance 107 may be based on the length of the sEWC 102 and a length between the end portion of the handle 105*a-d* or the fixing member 103*a*-103*d* and the distal end portion of the LG 101*a* or the other medical tools 101*b*-101*d*. In aspects, the handles 105*a*-105*d* may include control objects, e.g., a button or a lever, for controlling operation of the medical tools 101*a*-101*d*.

In some aspects, the position of the fixing member 105*a*-105*d* along the length of the medical tools 101*a*-101*d* may be adjustable so that the user can adjust the distance by which the distal end portion of the LG 101*a* or the medical tools 101*b*-101*d* extend beyond the distal end portion of the sEWC 102. The position and orientation of the LG sensor 104*a* relative to a reference coordinate system within an electromagnetic field can be derived using an application executed by the computer system 122. In some aspects, the sEWC 102 may act as the LG 101*a*, in which case the LG 101*a* may not be used. In other aspects, the sEWC 102 and the LG 101*a* may be used together. For example, data from the sensors 104*a* and 104*b* may be fused together. Catheter guide assemblies 110 are currently marketed and sold by Medtronic PLC under the brand names SUPERDIMENSION® Procedure Kits, or EDGE™ Procedure Kits, and are contemplated as useable with the disclosure.

The system 100 generally includes an operating table 112 configured to support a patient P; a bronchoscope 108 configured for insertion through patient P's mouth into patient P's airways; monitoring equipment 114 coupled to bronchoscope 108 (e.g., a video display for displaying the video images received from the video imaging system of bronchoscope 108); and a tracking system 115 including a tracking module 116, reference sensors 118, and a transmitter mat 120 or a transmitter board. The transmitter mat 120 may include incorporated markers. The system 100 further includes a computer system 122 for on which software and/or hardware are used to facilitate identification of a target, planning a pathway to the target, navigating a medical device to the target, and/or confirmation and/or determination of placement of the sEWC 102, or a suitable device therethrough, relative to the target.

As noted above, an imaging system 124 capable of acquiring fluoroscopic images or video or CBCT images of the patient P is also included in the system 100. The images, sequence of images, or video captured by the imaging system 124 may be stored within the imaging system 124 or transmitted to the computer system 122 for storage, processing, and display. Additionally, the imaging system 124 may move relative to the patient P so that images may be acquired from different angles or perspectives relative to patient P to create a sequence of images, such as fluoroscopic video.

The pose of the imaging system 124 relative to patient P and while capturing the images may be estimated via markers incorporated with the transmitter mat 120, in the operating table 112, or a pad (not shown) placed between the patient and the operating table 112. The markers are positioned under patient P, between patient P and operating table 112 and between patient P and a radiation source or a sensing unit of the imaging system 124. The markers may have a symmetrical spacing or may have an asymmetrical spacing, a repeating pattern, or no pattern at all. The imaging system 124 may include a single imaging system or more than one imaging system. When a CBCT system is employed, the captured images can be employed to confirm the location of the sEWC 102 and/or one of the medical tools 101*a*-101*d* within the patient, update CT-based 3D modeling, or replaced pre-procedural 3D modeling with intraprocedural modeling of the patient's airways and the position of the sEWC 102 within the patient.

The computer system 122 may be any suitable computing system including a processor and storage medium, such that the processor is capable of executing instructions stored on the storage medium. The computer system 122 may further include a database configured to store patient data, CT data sets including CT images, CBCT images and data sets, fluoroscopic data sets including fluoroscopic images and video, fluoroscopic 3D reconstructions, navigation plans, and any other such data. Although not explicitly illustrated, the computer system 122 may include inputs, or may otherwise be configured to receive, CT data sets, fluoroscopic images or video, and other suitable imaging data. Additionally, the computer system 122 includes a display configured to display graphical user interfaces. The computer system 122 may be connected to one or more networks through which one or more databases may be accessed by the computer system 122.

With respect to the navigation phase, a six degrees-of-freedom electromagnetic locating or tracking system 115, or other suitable system for determining position and orientation of a distal portion of the sEWC 102 (e.g., Fiber-Bragg flex sensors), is utilized for performing registration of pre-procedure images (e.g., a CT image data set and 3D models derived therefrom) and the pathway for navigation with the patient as they are located on operating table 112.

In an EMN-type system, the tracking system 115 may include the tracking module 116, the reference sensors 118, and the transmitter mat 120 (including the markers). The tracking system 115 is configured for use with a locatable guide, and particularly the LG sensor. As described above, the medical tools, e.g., the locatable guide 101*a* with the LG sensor 104*a*, are configured for insertion through the sEWC 102 into patient P's airways (either with or without the bronchoscope 108) and are selectively lockable relative to one another via a locking mechanism, e.g., the bronchoscope adapter 109. The transmitter mat 120 is positioned beneath patient P. The transmitter mat 120 generates an electromagnetic field around at least a portion of the patient P within which the position of the LG sensor 104*a*, the sEWC sensor 104*b*, and the reference sensors 118 can be determined through use of a tracking module 116. An additional electromagnetic sensor 126 may also be incorporated into the end of the sEWC 102. The additional electromagnetic sensor 126 may be a five degree-of-freedom sensor or a six degree-of-freedom sensor. One or more of the reference sensors 118 are attached to the chest of the patient P.

Registration refers to a method of correlating the coordinate systems of the pre-procedure images, and particularly a 3D model derived therefrom, with the patient P's airways as, for example, observed through the bronchoscope 108 and allow for the navigation to be undertaken with accurate knowledge of the location of the LG sensor within the patient and an accurate depiction of that position in the 3D model. Registration may be performed by moving the LG sensor through the airways of the patient P. More specifically, data pertaining to locations of the LG sensor, while the locatable guide is moving through the airways, is recorded using the transmitter mat 120, the reference sensors 118, and the tracking system 115. A shape resulting from this location data is compared to an interior geometry of passages of the 3D model generated in the planning phase, and a location correlation between the shape and the 3D model based on the comparison is determined, e.g., utilizing the software on the computer system 122. The software aligns, or registers, an image representing a location of LG sensor with the 3D model and/or two-dimensional images generated from the three-dimension model, which are based on the recorded location data and an assumption that LG remains located in non-tissue space in patient P's airways. Alternatively, a manual registration technique may be employed by navigating the bronchoscope 108 with the LG sensor to pre-specified locations in the lungs of the patient P, and manually correlating the images from the bronchoscope 108 to the model data of the 3D model.

Though described herein with respect to EMN systems using EM sensors, the instant disclosure is not so limited and may be used in conjunction with flexible sensor, shape sensors such as Fiber-Bragg gratings, ultrasonic sensors, or any other suitable sensor that does not emit harmful radiation. Additionally, the methods described herein may be used in conjunction with robotic systems such that robotic actuators drive the sEWC 102 or bronchoscope 108 proximate the target.

At any point during the navigation process, tools such as a locatable guide 101*a*, a therapy tool (e.g., a microwave ablation tool 101*b* or a forceps 101*d*), a biopsy tool (e.g., a biopsy needle 101*c*), may be inserted into and fixed in place relative to the sEWC 102 to place one of the tools 101*a*-101*d* proximate the target using position information from the sEWC 102. The position information from the sensors 104*b* and/or 126 of the sEWC 102 may be used to calculate the position of the distal tip or distal end portion of any of the tools 101*a*-101*d*.

To ensure the accuracy of the position calculations, the tools 101*a*-101*d* are each designed to extend a predetermined distance from the distal end of the sEWC 102 and at least the distal portions of the tools 101*a*-101*d* that extend from the sEWC 102 are designed to be rigid or substantially rigid. The predetermined distance may be different depending on one or more of the design of the tools 101*a*-101*d*, the stiffnesses of the tools 101*a*-101*d*, or how each of the tools 101*a*-101*d* interact with different types of tissue. The tools 101*a*-101*d* may be designed or characterized to set the predetermined distance to ensure deflection is managed (e.g., minimized) so that the virtual tools and environment displayed to a clinician are an accurate representation of the actual clinical tools and environment.

Calculating the position of the distal end portion of any of the tools 101*a*-101*d* may include distally projecting the position information from the sensors 104*b* and/or 126 according to tool information. The tool information may include one or more of the shape of the tool, the type of tool, the stiffness of the tool, the type or characteristics of the tissue to be treated by the tool, or the dimensions of the tool.

With respect to the planning phase, the computer system 122, or a separate the computer system not shown, utilizes previously acquired CT image data for generating and viewing a 3D model or rendering of patient P's airways, enables the identification of a target (automatically, semi-automatically, or manually), and allows for determining a pathway through patient P's airways to tissue located at and around the target. More specifically, CT images acquired from CT scans are processed and assembled into a 3D CT volume, which is then utilized to generate a 3D model of patient P's airways. The 3D model may be displayed on a display associated with the computer system 122, or in any other suitable fashion. Using the computer system 122, various views of the 3D model or enhanced two-dimensional images generated from the 3D model are presented. The enhanced two-dimensional images may possess some 3D capabilities because they are generated from 3D data. The 3D model may be manipulated to facilitate identification of target on the 3D model or two-dimensional images, and selection of a suitable pathway through patient P's airways to access tissue located at the target can be made. Once selected, the pathway plan, the 3D model, and the images derived therefrom, can be saved, and exported to a navigation system for use during the navigation phase(s). The ILLUMISITE software suite currently sold by Medtronic PLC includes one such planning software.

Figure 2:
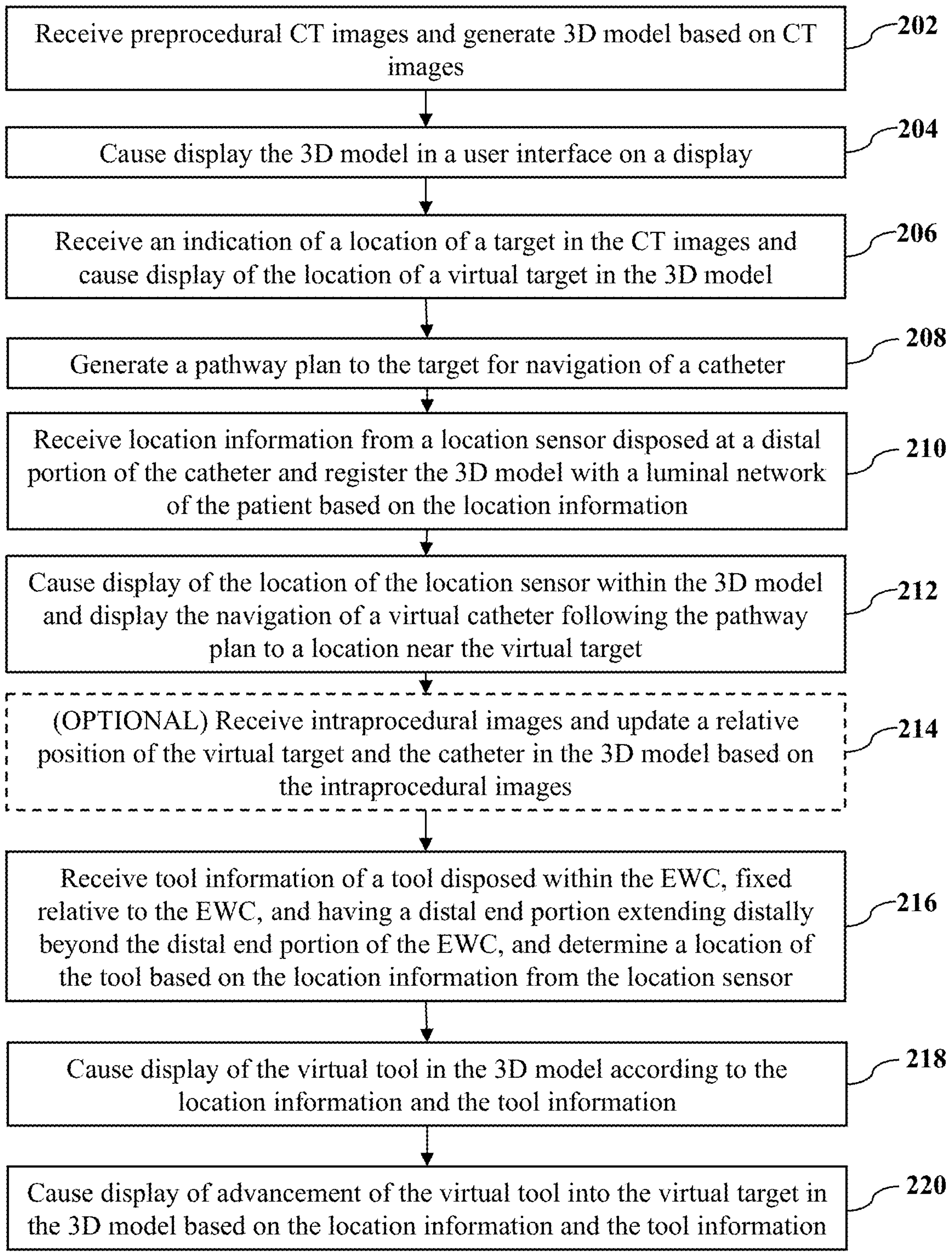
FIGS. 2 and 3 are flowcharts that illustrate examples of methods for navigating a medical tool to a target in accordance with this disclosure.

FIG. 2 depicts an example of a method of using the systems described herein. Those of skill in the art will recognize that one or more of the blocks of the method depicted in FIG. 2 may be omitted without departing from the scope of the disclosure. The method 200 starts with receiving preprocedural CT images and generating a 3D model based on the preprocedural CT images at block 202. At block 204, the 3D model and individual CT images (e.g., coronal, axial, sagittal views) can be displayed in a user interface allowing a user to manually inspect the CT images and to determine the location of a target. Alternatively, a software application may automatically detect the target.

At block 206, the system receives an indication of the location of the target. This may be the result of manual marking by a user manipulating the 3D model or CT images in a user interface, or it may be the result of a user accepting as accurate an automatic identification of a target by the application. Once the indication of the location of the target is received, the location of a virtual target is displayed in a 3D model on the user interface. Next, at block 208, a pathway to the target may be generated for navigation of the sEWC 102. As an example, the closest airway to the target may be identified and once identified, a pathway from that closest airway to the trachea may be automatically generated. Once both the location and pathway to the target are identified, the clinician is ready to conduct a procedure.

At block 210, following placement of a patient P on an operating table 112, and insertion of sEWC 102 and the associated sensor 104*b*, 126 into the airways of the patient P, the application receives one or more sensor signals from one or more of the sensor 104*b*, 126 which indicate the location of the sEWC 102 as the sEWC 102 is navigated through a luminal network of a patient. At block 210, the application also registers the 3D model and/or the CT images with the luminal network of the patient P. Receipt of the location information from one or more of the sensors 104*b*, 126 as the sEWC 102 is moved through at least a portion of the airways enables registration of the 3D model and/or the CT images with the patient's actual lungs as they are presented on the operating table 112. Once the patient's lungs are registered to the 3D model and/or the CT images, the location of the sEWC 102 and particularly the sensor 104*b*, 126 is displayed in the 3D model at block 212. This displayed position may substantially correspond to the actual position of the sEWC 102 within the lungs of the patient.

As the sEWC 102 is advanced into patient P, the position of the sensor 104*b*, 126 is displayed in the 3D model following the pathway plan to navigate the sEWC 102 to a location near the target at block 212. Once proximate the target, the imaging system 124 may be deployed and intraprocedural images captured and transmitted to the application at optional block 214. Block 214 may be optional in the situation where the CT-to-body divergence is at a minimum. In this way, radiation exposure may be reduced. These intraprocedural images can be employed to determine the positions of the sEWC 102 and sensor 104*b*, 126 relative to the target. Also, at block 214, the position of the virtual sEWC relative to the target is updated in the 3D model. Next, tool information of one of the tools 101*a*-101*d* disposed within the sEWC 102, fixed relative to the sEWC 102, and having a distal end portion extending distally beyond the distal end portion of the sEWC 102 is received at block 216. For example, the tool information may be received via text input to fields of a user interface. Alternatively, the tool information may be acquired from a pattern on the tool, e.g., a barcode or a QR code, or from an RFID tag disposed on or in the tool. The tool information may include one or more of dimensions of the tool, defining characteristics of the tool, or the predetermined distance and/or angle between a distal tip, portion, or tips (e.g., in the case of a forceps) and the distal end portion of the sEWC.

Then, after the tool is guided through and fixed in place with respect to the sEWC 102, the location information and the tool information is received and a location of the tool, e.g., a location of a portion, distal portion, or tip of the tool, is determined based on the location information from an EM sensor disposed at a distal portion of the sEWC 102 and the tool information at block 216. For example, a location of a tip of the tool may be calculated by projecting the location information from the EM sensor to a tip of the tool based on a distance and/or an angle of the tool information. The tool information may also include dimension information, which may be used to construct a virtual representation or model of the tool and display the virtual representation or model of the tool in the EMN display window or screen. As navigation is continued until the sEWC 102 is proximate the target, the virtual tool is displayed in the 3D model based on the location information and the tool information at block 218. At block 220, advancement of the virtual tool, e.g., a distal end portion of the tool, into the virtual target is displayed in the 3D model based on the location information and the tool information. The 3D model may be displayed in a user interface, e.g., the user interface 400 of FIG. 4, as the sEWC 102 is advanced based on the location information from one or more of the sensors 104*b*, 126 of the sEWC 102 and the tool information.

In some aspects, a user interface may be displayed for inputting sEWC and/or medical tool information, which may be used together with the position information of one or more of the sensors 104*b*, 126 of the sEWC 102 to calculate or project the position of the distal end portion of one of the medical tools 101*a*-101*d*. The user interface may include a prompt and a text field for inputting the sEWC identification number. The sEWC identification number input to the text field may be used to search a database for information relating to the sEWC 102 corresponding to the sEWC identification number input to the text field. The user interface may also include an alternative prompt and a text field for inputting information relating to the sEWC 102, which may be printed on the sEWC 102 or packaging associated with the sEWC 102.

The user interface may also include a prompt and a text field for inputting the tool identification number. The tool identification number input to the text field may be used to search a database for information relating to the tool corresponding to the tool identification number input to the text field. The user interface may also include an alternative prompt and a text field for inputting information relating to the tool, which may be printed on the tool or packaging associated with the tool.

Figure 3A:
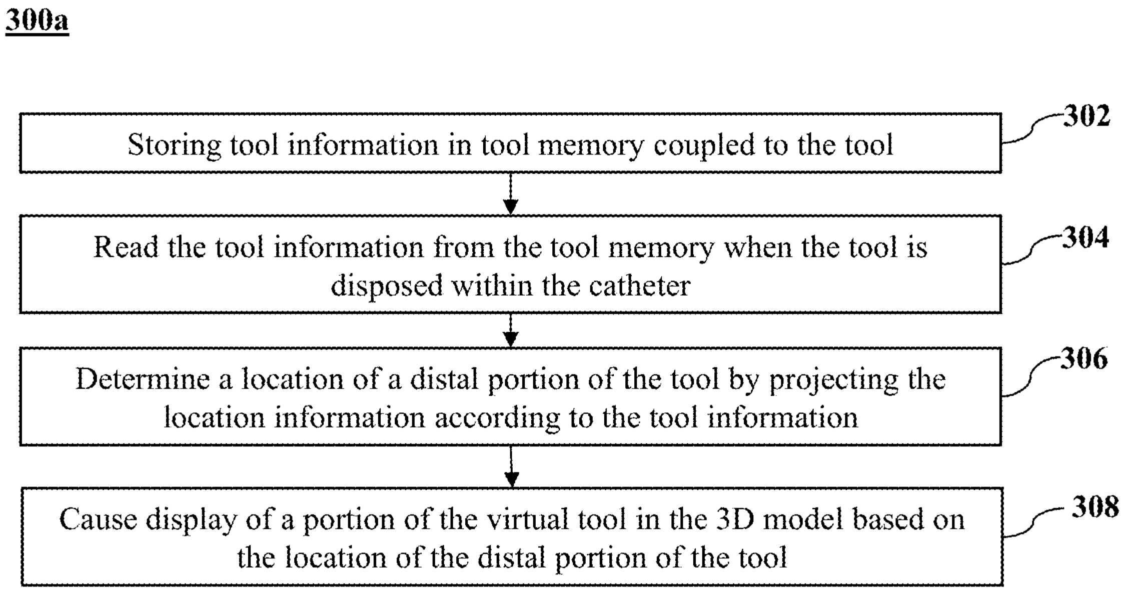

FIG. 3A is a flowchart that illustrates an example of a method for acquiring tool information and using that information to calculate the location of a distal portion of a tool. At block 302, tool information is stored in tool memory, e.g., an electronic chip or an RFID tag, coupled to the tool. At block 304, the tool information is read from the tool memory when the tool is disposed within the catheter. Alternatively, the tool information may be acquired from a code, e.g., QR code, disposed on the surface of the tool. At block 306, a location of a distal portion of the tool is determined by projecting the location information according to the tool information. And then, at block 308, a portion of the virtual tool is displayed in the 3D model based on the location of the distal portion of the tool.

Figure 3B:
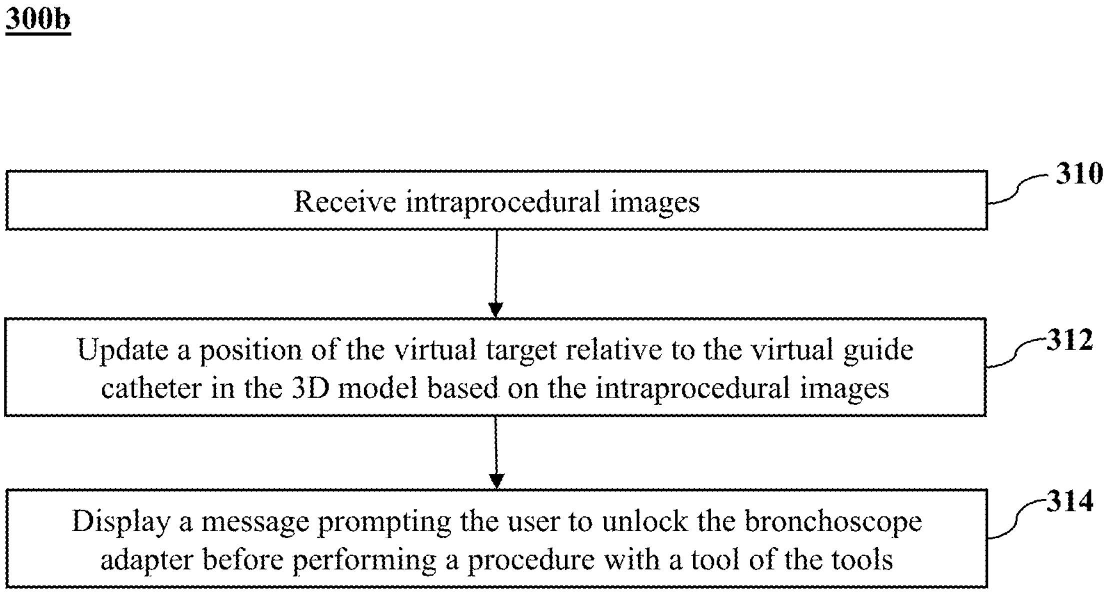

FIG. 3B is a flowchart that illustrates an example of an optional method for updating a virtual target relative to the virtual tool using intraprocedural images, e.g., intraprocedural C-arm fluoroscope images. This method may be performed after the sEWC 102 is navigated near the target in order to confirm that the registration between the CT images and the actual luminal network is still accurate. At block 310, intraprocedural images are received. At block 312, a position of the virtual target relative to the virtual guide catheter in the 3D model is updated based on the intraprocedural images Then, at block 314, a message prompting the user to unlock the bronchoscope adapter is displayed before performing a procedure with one of the tools 101*a*-101*b*.

The 3D modeling and pathway generation of the disclosure may be performed by a software application stored in a memory on the computer system 122 that when executed by a processor performs a variety of steps as described herein to generate the outputs displayed in a user interface. The 3D model is of the airways and the vasculature around the airways and generated, for example, from a pre-procedure CT images of the patient's lungs. Using segmentation techniques, the 3D model is defined from the CT image data set and depicts the airways in one color, the veins in a second color, and the arteries in a third color to assist the surgeon in distinguishing the portions of the anatomy based on color.

The application generating the 3D model may include a CT image viewer (not shown) enabling a user to view the individual CT images (e.g., 2D slice images from the CT image data) prior to generation of the 3D model. By viewing the CT images the clinician or other user may utilize their knowledge of the human anatomy to identify one or more targets in the patient. The clinician may mark the position of this target or suspected target in the CT images. If the target is identified in for example an axial slice CT image, that location may also be displayed in for example sagittal and coronal views. The user may then adjust the identification of edges of the target in all three views to ensure that the entire target is identified. As will be appreciated, other views may be viewed to assist in this process without departing from the scope of the disclosure. The application utilizes this indication of location provided by the clinician to generate and display an indicator of the location of the target in the 3D model. In addition to manual marking of the location of the target, there are a variety of known automatic target identification tools that are configured to automatically process the CT image scan and to identify the suspected targets.

Once the target is identified, the pathway planning software allows the user to identify an airway proximate the target in, for example, a 2D slice of the 3D volume of the CT image data set. When an airway is identified, the pathway planning software may automatically generate a pathway from the target, and specifically the identified airway proximate the target, to the trachea. This can be achieved using an algorithm that ensures that at every advancement of the pathway from the target to the trachea, the diameter of the airway increases relative to the prior portion of the airway. As will be appreciated, the planning software may also automatically identify the closest airway to the target and generate the pathway from the target to the trachea to be accepted by a clinician.

Figure 4:
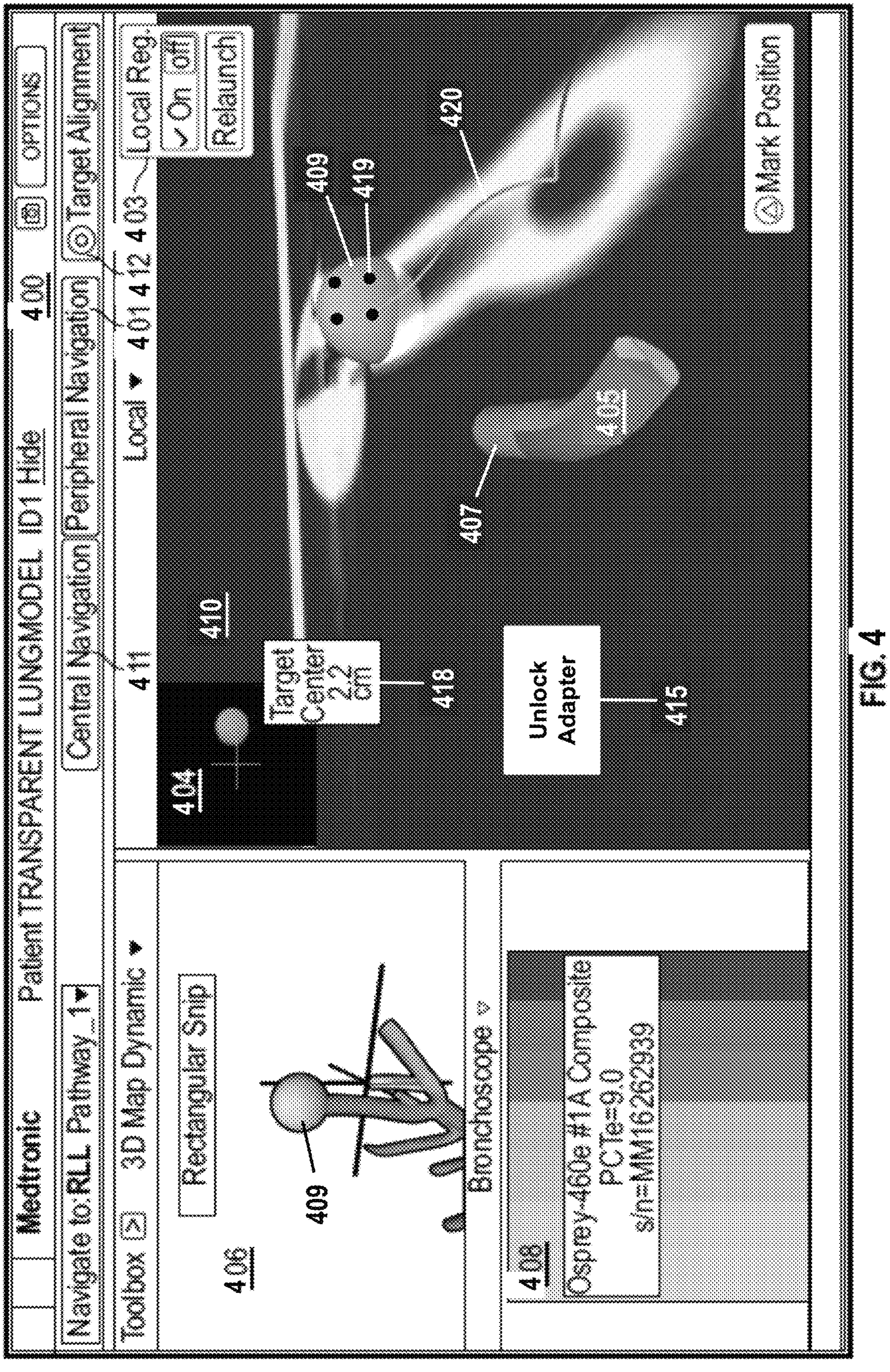
FIG. 4 is a diagram that illustrates a user interface for visualizing intraluminal navigation of a medical tool to a target via an sEWC in accordance with this disclosure.

After identifying a target, e.g., a tumor, and determining a pathway to the target, the computer system 122 is used to guide navigation of the sEWC 102 to the target. As noted above, the first step of such navigation is registration of the 3D model and therewith the data identified above, with the patient P as they are located on the operating table 112. Following registration of the patient P to the image data and pathway plan, a user interface 400 as shown in FIG. 4 is displayed on the computer system 122 allowing the clinician to advance the sEWC 102 into the airways of the patient P and have the movements of the sEWC 102 and movements of the distal end portion of the medical tool replicated in the 3D model.

The user interface 400 includes a variety of features and views that are common to lung navigation applications. These include a bronchoscopic view 408 depicting the view from a bronchoscope, where one is employed. A 3D map view 406 provides a perspective view of the 3D model of the luminal network and the location of the sEWC 102 as it is navigated through the patient P towards the target. A variety of buttons enable changing the primary view 410 displayed in the user interface 400. These include a central navigation button 411, a peripheral navigation button 401, and a target alignment view button 412.

As the navigation of the sEWC 102 changes from the central airways to the peripheral airways the appropriate button may be selected to change the primary view 410. This may also be automatic as the location of the sEWC 102 is detected. As shown in FIG. 4, the target alignment view 412 has been selected. Once selected, a target window 404 is displayed overlaid on the primary view 410. Alternatively, the target window 404 may not be overlaid on any of the other views of the user interface 400. The target window 404 depicts crosshairs, the virtual target 409, and a distance indicator 418 displaying the distance from the location of the end of the virtual tool 407, which is calculated based on the detected location of the end of the sEWC 102, to the virtual target 409. As shown in the user interface 400 of FIG. 4, the virtual tool 407 has been navigated via the sEWC 102 to within about 5 cm of the virtual target 409 to biopsy or treat another segment of the virtual target 409. Also depicted in the primary view 410 is the planned pathway 420 to the virtual target 409. The virtual target 409 may be segmented and show segments that have already been biopsied or otherwise treated by the virtual tool 407. For example, the virtual target 409 may show points 419 indicating locations where the virtual tool 407 has biopsied or treated the virtual target 409. This enables a clinician to uniformly treat or biopsy the target 409. In The primary view 410 also shows the distal end portion of the virtual sEWC 405 and the distal end portion of the virtual tool 407 extending beyond the distal end portion of the virtual sEWC 405. The primary view 410 may also display a message 415 to the clinician to unlock the bronchoscope adapter so that the clinician can control the sEWC 102 to move the distal end portion of the virtual tool 407 towards and into or adjacent to the virtual target 409 to perform a biopsy or treatment procedure.

A local registration may be undertaken via the buttons 403. The local registration is useful in eliminating any divergence such as CT-to-body divergence, but also any divergence in the position of the target caused by shrinkage related to therapy of other targets, the insertion of tools into the airways, and the position of the patient P. A local registration employs the imaging system 124 to acquire intraprocedural images of the area proximate the end of the sEWC 405 and the virtual target 409. An initial step is to acquire a 2D fluoroscopic images of the sEWC 405 and mark the area of the sEWC 405. This helps to ensure that the imaging system 124 is properly focused on the sEWC 405. Next, a sequence of fluoroscopic images is captured by the imaging system 124 for example from about 25 degrees on one side of the AP position to about 25 degrees on the other side of the AP position and a fluoroscopic 3D reconstruction may be then generated by the computer system 122. The generation of the fluoroscopic 3D reconstruction is based on the sequence of fluoroscopic images and the projections of structure of markers incorporated within the transmitter mat 120 on the sequence of fluoroscopic images.

Following generation of the fluoroscopic 3D reconstruction, the sEWC 102 needs to be marked in two 2D images of the 3D reconstruction. The two images are taken from different portions of the fluoroscopic 3D reconstruction. The fluoroscopic images of the 3D reconstruction may be presented on the user interface in a scrollable format where the user is able to scroll through the slices in series if desired. Next the target needs to be marked in fluoroscopic 3D reconstruction. A scroll bar may be provided to allow the user to scroll through the fluoroscopic 3D reconstruction until the target is identified. In addition, the target may need to be marked in at two different perspectives. Once complete, the user-interface displays the entire fluoroscopic 3D reconstruction which may be viewed slice by slice to ensure that the target or lesion remains within the marker through the fluoroscopic 3D reconstruction.

After confirming that the target has been accurately marked the local registration process ends and the relative position of the virtual sEWC 405 in the 3D model and the pathway plan is updated to display the actual current relative position of the end of the virtual sEWC 405 and the target as it is in the patient.

In some aspects, the system 100 includes an ablation tool 101*b*, e.g., an ablation catheter, and the computer system 122 may execute an ablation planning feature. In the ablation planning feature, all of the data generated pre-procedurally related to the placement of the ablation catheter, the timing and power settings of the ablation and the duration of any pauses can be presented on the user-interface for the clinician as they are preparing to initiate the therapy portion of the procedure. In addition, this data can be overlaid on intraprocedural images (e.g., fluoroscopic or CBCT images). These may be additional intraprocedural images acquired after the local registration. As an example, the place for insertion of the ablation or biopsy catheter into the target can be overlaid on the intraprocedural images so that placement is accurate prior to insertion of an ablation catheter or a biopsy catheter. In some cases, the intraprocedural images may be live fluoroscopic video such that at least a portion of the advancement of the ablation catheter into the target can be observed as the ablation catheter intersects with the overlaid marked location from the ablation planning feature.

Once properly placed, and again before insertion of the ablation catheter, an ablation zone specified in the ablation planning feature can be overlaid and compared to the tissue as it presents itself in the intraprocedural images. As is known, the position of tissue during the procedure is expected to be different from its position during pre-procedure images. Indeed, this is the rationale for the local registration. Thus, by overlaying the anticipated ablation zone on the intraprocedural images the user may edit the ablation zone prior to insertion of the ablation catheter into the sEWC 102 and the target.

Further, as the ablation catheter is inserted into the sEWC 102, a further set of intraprocedural images may be acquired from the imaging system 124. At this point the ablation catheter may be segmented from the images to confirm placement in the correct location and at the correct depth in the target and the anticipated ablation zone, as updated or altered can be overlaid onto these images prior to initiating the ablation. This provides one more opportunity to adjust or alter the ablation zone, the margin, the placement of the ablation catheter, the power, duration, and other factors prior to in initiating therapy. Once the ablation zone, as it is overlaid on the image of the target in the intraprocedural image, is deemed acceptable, the therapy may be commenced (e.g., application of microwave energy, RF energy, etc.).

In aspects, key structures may be overlayed on the intraprocedural images. By observing the overlay of these key structures on the intraprocedural images (e.g., fluoroscopic or CBCT images) acquired by the imaging system 124 monitoring of the lungs can be undertaken during the procedure. This monitoring can be either manual or automatic and enables determination of a level of divergence between the position of these key structures in the pre-procedure images and 3D model to the intraprocedural images. That divergence may be a result of movement of the patient or the result of some intraprocedural aspects such as insertion of one or more of the tools 101*a*-101*d* through the sEWC 102. Further, the divergence may be an indicator of atelectasis in one or more lobes of the lung or movement of the target. As a result of this detected divergence, an indicator may appear on the user interface directing the user to undertake another scan either with the imaging system 124 or the same imaging modality of the pre-procedure imaging to confirm the divergence and assess the changing conditions of the anatomy of the patient.

As noted herein, a variety of intraprocedural imaging may optionally be employed during the treatment of a patient. One aspect of this disclosure is the ability to register the pre-procedure CT images and any intraprocedural images. In some instances, this allows data from the planning phase to be overlaid on fluoroscopic images. Additionally, in the case of any intraprocedural CT imaging, including CBCT imaging, all of the pathway plan and ablation plan can be brought from one such CT image data set to a second CT image data set based on the registration. This eliminates the need for additional planning being needed interprocedurally. The registration may be based on the structure of the airways, as well as other harder less movable tissues such as ribs that are observable in the CT images. Where appropriate additional local registration as described above may also be employed to eliminate any errors in the registration at or near the target.

With respect to the optional intraprocedural imaging using the imaging system 124, a variety of techniques are contemplated in connection with the disclosure. As noted above the imaging system 124 may be a C-arm fluoroscope, a CBCT imaging system, or a 3D fluoroscopic imaging system. In instances where the imaging system 124 is a CBCT imaging system, the local registration process described above for updating the position of the sEWC 102 relative to the target within the patient can also be employed. In one aspect of this application, a low dose CBCT scan can be utilized since a high-resolution scan is not required for the local registration. The low dose scan reduces the amount of radiation that the patient P absorbs during the procedure. It is always desirable to reduce the amount of radiation both the patient P and the doctors and nurses are exposed to during a procedure. In some instances, where there is integration between the imaging system 124 and the system 100, the imaging system 124 may receive input directing the imaging system 124 to specific locations to conduct the imaging.

Further aspects of the intraprocedural imaging are related to additional ways of reducing the amount of radiation to the patient and clinicians. CBCT imaging systems have a frame rate at which images are captured. By capturing images at relatively high frequency and at small angular displacement between the images, a very high resolution image data set can be captured by the CBCT imaging system. However, such high resolution is not required in all instances. One aspect of the disclosure is directed to directing the imaging system 124 to skip frames. Depending on the setting, this could be skipping every other frame, every third frame, every forth frame, etc. By doing so, when considering the hundreds or even thousands of frames which make up a radiographic image, the overall exposure to radiation can be reduced.

Alternatively, particularly where a high resolution image is desired, for example, the sEWC 102 or the tools 101*a*-101*d* may be placed within the target focusing the imaging system 124 onto just the tissue of interest. The rays of the imaging system 124, e.g., CBCT system, can be collimated to narrow the area of imaging to just the tissue or area of interest and not the entire lung of the patient. In this way, the amount of total radiation and the area that the radiation is directed are both reduced. Yet, the images produced from this focused imaging has a very high resolution allowing for detailed analysis of, for example, the tissue around the target or proper placement of the sEWC 102 and the tools 101*a*-101*d*.

The preprocedural CT images that are acquired to perform the planning of the procedure are typically taken while the patient P is in a breath hold condition. This ensures that the lungs are fully inflated providing greater clarity of images. However, during a procedure, the patient P is typically maintained in tidal volume breathing. This minimizes stress on the patient P, ensuring adequate oxygen saturation during the procedure, and minimizes the movement of the lungs and therewith the target as a result of breathing. In connection with both biopsy and other tissue treatment, rather than continue at with tidal volume breathing during the tissue treatment or even during the insertion of the tool into the target, the imaging can be triggered at a specified positive end-expiratory pressure (PEEP), that is the positive pressure that will remain in the airways at the end of the respiratory cycle. The imaging may be performed at either inspiration or expiration at the predetermined PEEP or may be conducted during a breath hold at the predetermined PEEP. The result is that at the time of insertion ablation catheter, accurate imagining may be acquired with limited movement of the target and the ablation catheter or biopsy catheter during the insertion. The imaging system 124 may be configured to automatically initiate imaging as the lung pressure approaches the specified PEEP and terminate imaging after reaching some threshold lung pressure. In this manner, the imaging system 124, e.g., a CBCT system, may be cycled on and off during the ablation procedure at specified times where the target is expected to be in the same position. This allows for a consistent comparison of the ablation volume to the target and the planned ablation volume.

As will be appreciated integration of the controls of the imaging system 124 and the lung navigation user interface 400 can greatly enhance the functionality of the overall system. For example, one or more buttons may be generated by an application stored in the memory of the computer system 122. Those buttons transmit signals to the imaging system 124, for example, to initiate imaging of the patient. In addition, the buttons may transmit signals to the imaging system 124 to control its position relative to the patient. In one embodiment, the position and orientation of the distal portion of the sEWC 102, that is known to the navigation application, for example via the interaction of the sensors 104*b*, 126 and the transmitter mat 120. This position information can be employed to generate a signal that is transmitted to the imaging system 124 to orient the imaging system 124 in such a way that the images generated are centered on the sEWC 102. In instances where the sEWC 102 has been navigated proximate the target, the centering of the imaging on the sEWC 102 ensures that the target is visible in the images.

As an example, having determined the position of the sEWC 102, the navigation application presents on the user interface one or more buttons to drive the imaging system 124 to an optimal position for imaging the end of the sEWC 102 and the target. Once so positioned, the imaging system 124 performs the scan, and then transmits the acquired images to the navigation application to display the acquired images or a 3D model generated from the images and updating the navigation user interface 400.

Though described herein as being executed through the use of one or more buttons displayed on the user interface, the disclosure is not so limited. The process may be automated and signals may be generated upon reaching certain milestones during the navigation. For example, upon navigating the sEWC 102 proximate the target, a signal may be transmitted to the imaging system 124 to stop the imaging system 124 automatically in order to begin EM tracking of the tip of the sEWC and calculating the position of the tip or end portion of one of the tools 101*a*-101*d*.

As described herein, the methods and systems are in aspects related to placement of tools, such as ablation tools 101*b*, in a lesion or tumor of a patient. In particular the ablation tools are navigated through the luminal network of the airways and placed within the tumor or lesion to ablate or kill the cells of the lesion or tumor and a margin around the lesion or tumor to stop the growth of the disease at that location. The EMPRINT™ ablation platform offered by Medtronic is one system for performing an ablation that produces spherical ablations. Other ablation systems such as radio frequency (RF), ethanol, cryogenic, and others may be used with the systems and methods described herein, and the navigation is substantially as described herein above.

Figure 5:
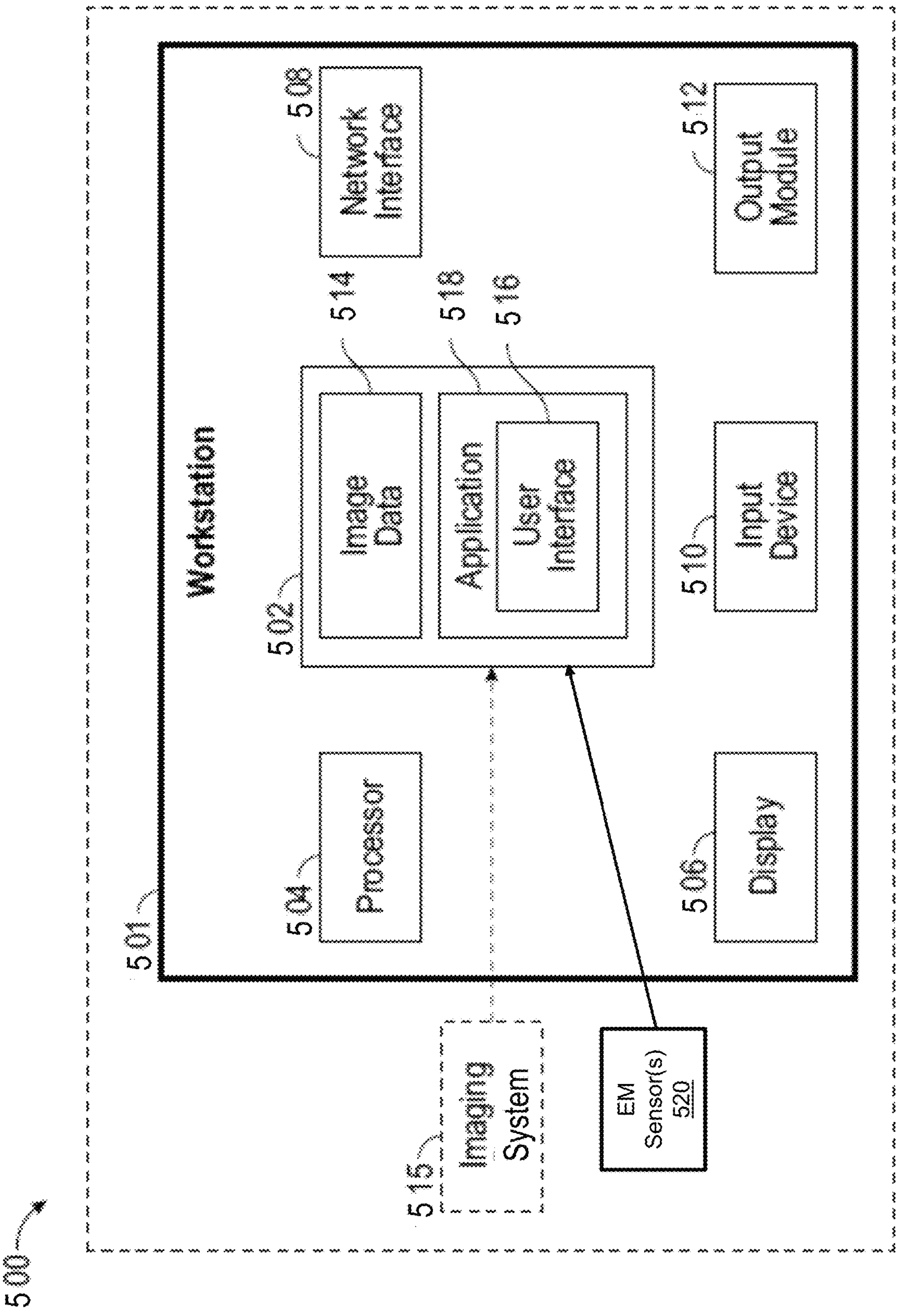
FIG. 5 is a schematic view that illustrates a computer system in accordance with this disclosure.

Reference is now made to FIG. 5, which is a schematic diagram of a system 500 configured for use with the methods of the disclosure including the method of FIG. 2. The system 500 may include a workstation 501, and optionally an imaging system 515, e.g., a fluoroscopic imaging system and/or a CT imaging system for capturing preoperative 3D images. In some aspects, the workstation 501 may be coupled with the imaging system 515, directly or indirectly, e.g., by wireless communication. The workstation 501 may include a memory 502, a processor 504, a display 506 and an input device 510. The processor 504 may include one or more hardware processors. The workstation 501 may optionally include an output module 512 and a network interface 508. The memory 502 may store an application 518 and image data 514. The application 518 may include instructions executable by the processor 504 for executing the methods of the disclosure including the method of FIG. 2.

The application 518 may further include a user interface 516. The image data 514 may include preoperative CT image data, fluoroscopic image data, or fluoroscopic 3D reconstruction data. The processor 504 may be coupled with the memory 502, the display 506, the input device 510, the output module 512, the network interface 508, and the imaging system 515. The workstation 501 may be a stationary computer system, such as a personal computer, or a portable computer system such as a tablet computer. The workstation 501 may embed multiple computers.

The memory 502 may include any non-transitory computer-readable storage media for storing data and/or software including instructions that are executable by the processor 504 and which control the operation of the workstation 501, process data from one or more EM sensors 520 disposed in or on the sEWC, e.g., at a distal end portion of the sEWC, to track the position of the sEWC and calculate or project the position of a distal end portion of a medical tool at a fixed position within the sEWC, and, in some aspects, may also control the operation of the imaging system 515. The imaging system 515 may be used to capture a sequence of preoperative CT images of a portion of a patient's body, e.g., the lungs, as the portion of the patient's body moves, e.g., as the lungs move during a respiratory cycle. Optionally, the imaging system 515 may include a fluoroscopic imaging system that captures a sequence of fluoroscopic images based on which a fluoroscopic 3D reconstruction is generated and/or to capture a live 2D fluoroscopic view to confirm placement of the sEWC and/or the medical tool. In one aspect, the memory 502 may include one or more storage devices such as solid-state storage devices, e.g., flash memory chips. Alternatively, or in addition to the one or more solid-state storage devices, the memory 502 may include one or more mass storage devices connected to the processor 504 through a mass storage controller (not shown) and a communications bus (not shown).

Although the description of computer-readable media contained herein refers to solid-state storage, it should be appreciated by those skilled in the art that computer-readable storage media can be any available media that can be accessed by the processor 504. That is, computer readable storage media may include non-transitory, volatile and non-volatile, removable and non-removable media implemented in any method or technology for storage of information such as computer-readable instructions, data structures, program modules or other data. For example, computer-readable storage media may include RAM, ROM, EPROM, EEPROM, flash memory or other solid-state memory technology, CD-ROM, DVD, Blu-Ray or other optical storage, magnetic cassettes, magnetic tape, magnetic disk storage or other magnetic storage devices, or any other medium which may be used to store the desired information, and which may be accessed by workstation 501.

The application 518 may, when executed by the processor 504, cause the display 506 to present the user interface 516. The user interface 516 may be configured to present to the user a single screen including a three-dimensional (3D) view of a 3D model of a target from the perspective of a tip of a medical tool, a live two-dimensional (2D) fluoroscopic view showing the medical tool, and a target mark, which corresponds to the 3D model of the target, overlaid on the live 2D fluoroscopic view. The user interface 516 may be further configured to display the target mark in different colors depending on whether the medical tool tip is aligned with the target in three dimensions.

The network interface 508 may be configured to connect to a network such as a local area network (LAN) consisting of a wired network and/or a wireless network, a wide area network (WAN), a wireless mobile network, a Bluetooth network, and/or the Internet. The network interface 508 may be used to connect between the workstation 501 and the imaging system 515. The network interface 508 may be also used to receive the image data 514. The input device 510 may be any device by which a user may interact with the workstation 501, such as, for example, a mouse, keyboard, foot pedal, touch screen, and/or voice interface. The output module 512 may include any connectivity port or bus, such as, for example, parallel ports, serial ports, universal serial busses (USB), or any other similar connectivity port known to those skilled in the art. From the foregoing and with reference to the various figures, those skilled in the art will appreciate that certain modifications can be made to the disclosure without departing from the scope of the disclosure.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical tool.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A system for navigating to a target via a luminal network of a patient, the system comprising:

an extended working channel (EWC) including a location sensor disposed at a distal portion of the EWC;

at least one processor; and a memory coupled to the at least one processor and having stored thereon instructions, which when executed by the at least one processor, cause the at least one processor to:

receive preprocedural computed tomography (CT) images;

generate a three-dimensional (3D) model based on the CT images;

cause display of the 3D model in a user interface on a display operatively coupled to the at least one processor;

receive an indication of a location of a target in the CT images;

cause display of the location of the target in the 3D model;

generate a pathway plan to the target for navigation of the EWC;

receive location information from the location sensor as the EWC is navigated through a luminal network of a patient;

register the 3D model with the luminal network of the patient based on the location information;

cause display of the location of the location sensor within the 3D model that substantially corresponds to the location of the location sensor within the luminal network of the patient;

cause display of the navigation of the EWC following the pathway plan to a location near the target;

receive tool information of a tool disposed within the EWC, fixed relative to the EWC, and having a substantially rigid distal end portion extending distally beyond the distal end portion of the EWC by a predetermined distance;

determine a location of the distal end portion of the tool by projecting the location information from the location sensor distally along the predetermined distance;

cause display of a virtual tool in the 3D model according to the location information and the tool information;

cause display of a distal end portion of the virtual tool extending beyond a distal end portion of a virtual EWC based on the projected location of the distal end portion of the tool; and cause display of advancement of the virtual tool into the target in the 3D model based on the location information and the tool information.

2. The system of claim 1, wherein the tool includes a locatable guide tool including a second location sensor, an ablation tool, or a biopsy tool.

3. The system of claim 2, wherein the EWC includes an EWC handle, and wherein the tool includes:

a fixing member configured to mate with the EWC handle when the tool is disposed within the EWC and a distal portion of the tool extends beyond the distal portion of the EWC, and configured to fix the tool in place with respect to the EWC; and a handle for operating the tool.

4. The system of claim 1, wherein the distal portion of the EWC is curved, wherein instructions when executed by the at least one processor further cause the at least one processor to receive location information with six degrees of freedom.

5. The system of claim 1, wherein the instructions when executed by the at least one processor further cause the at least one processor to:

display a message prompting a user to lock a bronchoscope adapter;

receive intraprocedural images;

update a relative position of the target and the EWC in the 3D model based on the intraprocedural images; and display a message prompting the user to unlock the bronchoscope adapter.

6. The system of claim 5, wherein the intraprocedural images are C-arm fluoroscopic images, 3D fluoroscopic images, or cone beam CT images.

7. The system of claim 6, wherein the tool information is a tool type, tool characteristics, or tool dimensions, and wherein the instructions when executed by the at least one processor further cause the at least one processor to:

determine a location of a distal portion of the tool by projecting the location information according to the tool information; and cause display of a portion of the virtual tool in the 3D model based on the location of the distal portion of the tool.

8. The system of claim 6, further comprising:

a tool memory coupled to the tool and configured to store the tool information; and a tool memory reader configured to read the tool information from the tool memory, wherein the at least one processor is in operative communication with the tool memory reader, and wherein the instructions when executed by the at least one processor further cause the at least one processor to receive the tool information from the tool memory reader.

9. A method for navigating to a target via a luminal network, the method comprising:

receiving computed tomography (CT) images;

generating a three-dimensional (3D) model based on the CT images:

causing display of the 3D model in a user interface on a display;

receiving an indication of a location of a target in the CT images;

causing display of the location of the target in the 3D model;

generating a pathway plan to the target for navigation of a catheter;

receiving location information from a location sensor disposed at a distal portion of the catheter;

registering the 3D model with a luminal network of a patient based on the location information;

causing display of the location of the location sensor within the 3D model;

causing the display of the navigation of the catheter following the pathway plan to a location near the target;

receiving tool information of a tool disposed within the catheter, fixed in place relative to the catheter, and having a substantially rigid distal end portion extending distally beyond the distal end portion of the catheter by a predetermined distance;

determining a location of the distal end portion of the tool by projecting the location information from the location sensor distally along the predetermined distance;

causing display of at least a portion of a virtual tool in the 3D model based on the projected location and the tool information;

causing display of a distal end portion of the virtual tool extending beyond a distal end portion of a virtual catheter based on the projected location of the distal end portion of the tool; and causing display of advancement of the tool to the target in the 3D model based on the location information and the tool information.

10. The method of claim 9, further comprising displaying a distal end portion of the tool as the target is treated, ablated, sampled, or biopsied.

11. The method of claim 9, further comprising:

receiving intraprocedural images of the catheter and the target; and updating a location of the catheter relative to the target in the 3D model based on the intraprocedural images.

12. The method of claim 11, wherein receiving the intraprocedural images includes receiving 2D fluoroscopic images, 3D fluoroscopic images, or cone beam CT images.

13. The method of claim 11, further comprising causing display of at least a portion of the pathway plan, at least a portion of the tool, and the target on the intraprocedural images.

14. The method of claim 11, wherein the intraprocedural images are captured at a decreased radiation dose.

15. A system comprising:

a guide catheter configured for insertion into a luminal network of a patient;

a sensor coupled to the guide catheter for sensing a location of a distal end portion of the guide catheter within the luminal network of the patient;

tools configured to be inserted through the guide catheter such that a distal end portion of the tools extend distally beyond the distal end portion of the guide catheter, and configured to be fixed relative to the guide catheter during navigation of the guide catheter;

at least one processor;

a display operatively coupled to the at least one processor; and a memory coupled to the at least one processor and having stored thereon instructions, which when executed by the at least one processor, cause the at least one processor to:

cause display of a virtual target in a 3D model on the display;

receive location information from the sensor in the luminal network of the patient;

cause display of navigation of a virtual guide catheter near the virtual target in the 3D model based on the location information;

determine tool information from a tool inserted through the guide catheter, fixed in place relative to the guide catheter, and having a substantially rigid distal end portion extending distally beyond the distal end portion of the guide catheter by a predetermined distance;

determine a location of the distal end portion of the tool by projecting the location information from the sensor distally along the predetermined distance;

cause display, in the 3D model, of the distal end portion of a virtual tool based on the projected location and the tool information;

cause display of a distal end portion of the virtual tool extending beyond a distal end portion of a virtual guide catheter in the 3D model based on the projected location of the distal end portion of the tool; and cause display of operation of the virtual tool to perform a procedure on the virtual target in the 3D model based on updated location information and the tool information.

16. The system of claim 15, wherein the guide catheter is a smart extended working channel, and wherein the tools include at least two of a locatable guide, a forceps, a biopsy needle, or an ablation antenna.

17. The system of claim 15, further comprising a bronchoscope adapter configured to lock the guide catheter in place, wherein the instructions when executed by the at least one processor further cause the at least one processor to:

receive intraprocedural images;

update a position of the virtual target relative to the virtual guide catheter in the 3D model based on the intraprocedural images; and display a message prompting a user to unlock the bronchoscope adapter before performing a procedure with a tool of the tools.

18. The system of claim 15, wherein the tools include handles, respectively, and wherein lengths from distal end portions of the handles to the distal end portions of the tools are same lengths.

19. The system of claim 15, further comprising an electromagnetic generator configured to generate an electromagnetic field, wherein the sensor is an EM sensor configured to sense the electromagnetic field and output an electromagnetic field signal indicating the location of the EM sensor.

* * * * *